(12) United States Patent
Nakamura

(10) Patent No.: US 9,162,971 B2
(45) Date of Patent: Oct. 20, 2015

(54) METHODS FOR PRODUCING BICYCLIC COMPOUNDS VIA CLAISEN REARRANGEMENTS

(71) Applicant: Daiichi Sankyo Company, Limited, Tokyo (JP)

(72) Inventor: Yoshitaka Nakamura, Kanagawa (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

(21) Appl. No.: 14/100,402

(22) Filed: Dec. 9, 2013

(65) Prior Publication Data

US 2014/0094623 A1 Apr. 3, 2014

Related U.S. Application Data

(63) Continuation of application No. PCT/JP2012/064416, filed on Jun. 5, 2012.

(30) Foreign Application Priority Data

Jun. 8, 2011 (JP) ................. 2011-127958

(51) Int. Cl.
| | | |
|---|---|---|
| *C07C 227/22* | (2006.01) | |
| *C07C 227/18* | (2006.01) | |
| *C07C 229/32* | (2006.01) | |
| *C07C 51/38* | (2006.01) | |
| *C07C 45/51* | (2006.01) | |
| *C07C 45/41* | (2006.01) | |

(52) U.S. Cl.
CPC ............... *C07C 227/22* (2013.01); *C07C 45/41* (2013.01); *C07C 45/515* (2013.01); *C07C 51/38* (2013.01); *C07C 227/18* (2013.01); *C07C 229/32* (2013.01); *C07C 2102/20* (2013.01)

(58) Field of Classification Search
CPC ...... C07C 45/515; C07C 51/38; C07C 47/21; C07C 57/03; C07C 227/18; C07C 227/22; C07C 229/32; C07C 45/41; C07C 2102/20
USPC .......................................... 562/501; 568/356
See application file for complete search history.

(56) References Cited

U.S. PATENT DOCUMENTS

| 5,191,125 A | 3/1993 | Rosini et al. |
| 2003/0078300 A1 | 4/2003 | Blakemore et al. |
| 2003/0220397 A1 | 11/2003 | Bryans et al. |
| 2004/0152779 A1 | 8/2004 | Bryans et al. |
| 2006/0154929 A1 | 7/2006 | Anker et al. |
| 2010/0110361 A1 | 5/2010 | Matsuda et al. |
| 2010/0249229 A1 | 9/2010 | Shimada et al. |

FOREIGN PATENT DOCUMENTS

| CA | 2 756 750 A1 | 9/2010 |
| EP | 0 287 956 B1 | 11/1993 |
| EP | 0 521 571 B1 | 9/1995 |
| EP | 2 192 109 A1 | 6/2010 |
| WO | WO 2006/075596 A1 | 7/2006 |
| WO | WO 2009/041453 A1 | 4/2009 |
| WO | WO 2010/084798 A1 | 7/2010 |
| WO | WO 2010/110361 A1 | 9/2010 |

OTHER PUBLICATIONS

Matsuda-machine translation of WO2006/075596, published on Jul. 20, 2006, p. 1-16.*
Greene ("Greene's Protective Groups in Organic Synthesis, Fourth Edition" Ch. 1 and 2, p. 1-365, John Wiley and Sons, Ltd, Apr. 10, 2006, online ISBN: 9780470053485, DOI: 10.1002/0470053488).*
Inokuchi ("E- or Z-Selective Knoevenagel Condensation of Acetoacetic Derivatives: Effect of Acylated Substituent, that is, TEMPO and Amines, as an Auxiliary, and New Accesses to Trisubstituted E- and Z-2-Alkenals and Furans" J. Org. Chem, 2006, 71, 947-953).*
Beereboom, "The Cyclization of Geranic Acids. Preparation of a Cyclobutanone," *J. Org. Chem.*, 30(12):4230-4234 (1965).
Bryans et al., "Identification of Novel Ligands for the Gabapentin Binding Site on the $\alpha_2\delta$ Subunit of a Calcium Channel and Their Evaluation as Anticonvulsant Agents," *J. Med. Chem.*, 41:1838-1845 (1998).
Gee et al., "The Novel Anticonvulsant Drug, Gabapentin (Neurontin), Binds to the $\alpha_2\delta$ Subunit of a Calcium Channel," *J. Biol. Chem.*, 271:5768-5776 (1996).
International Search Report issued in PCT Application No. PCT/JP2012/064416 on Aug. 21, 2012, 3 pages.
Brannock, "Preparation of Substituted 4-Pentenals," *Journal of the American Chemical Society*, ACS Publications, U.S., (1959), 81:3379-3383.
Snider et al., "Type III Intramolecular [2+2] Cycloadditions of Vinylketenes," *J. Org. Chem.*, (1988), 53:5320-5328.
Thomson Scientific, London, GB, Database WPI XP002731609, Week 200660, "Manufacture of 2-allylcarboxylic acid compound useful as synthetic intermediate of (R)-2-propyl octanoic acid, involves reacting aldehyde in presence of acid catalyst and allyl alcohol, and converting obtained 2-allylcarbonyl compound," 7 pages, Jul. 20, 2006.
Whittaker et al., "Asymmetric synthesis towards (3Z,6R)-3-methyl-6-isopropenyl-3,9-decadien-1-yl acetate, a component of the California red scale pheromone," *Can. J. Chem.*, (1985), 63(11):2844-2852.
Supplementary European Search Report mailed Nov. 3, 2014, in European Application No. 12 79 6945, 7 pages.

* cited by examiner

*Primary Examiner* — Jafar Parsa
*Assistant Examiner* — Amy C Bonaparte
(74) *Attorney, Agent, or Firm* — Dorsey and Whitney LLP

(57) ABSTRACT

The problem to be solved by the present invention is to provide a method for producing a compound having excellent activity as an $\alpha_2\delta$ ligand. The solution thereto is a method for producing a compound represented by the general formula (VI) or a salt thereof using rearrangement reaction: [in the formula, $R^1$: a hydrogen atom or a C1-C6 alkyl group]

[Formula 1]

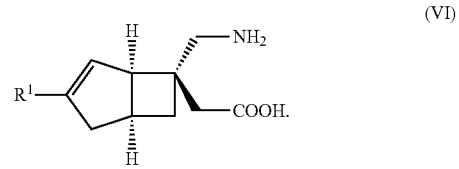

(VI)

8 Claims, No Drawings

METHODS FOR PRODUCING BICYCLIC COMPOUNDS VIA CLAISEN REARRANGEMENTS

This application claims the benefit under 35 U.S.C. §111 (a) as a continuation application of International Application No. PCT/JP2012/064416, filed Jun. 5, 2012, entitled "Method For Producing Bicyclic Compound Via Claisen Rearrangement," which claims priority to Japanese Patent Application No. 2011-127958, filed Jun. 8, 2011, the contents of all of which are hereby incorporated in their entirety by reference.

TECHNICAL FIELD

The present invention relates to a method for producing a bicyclic γ-amino acid derivative or a pharmacologically acceptable salt thereof, particularly, a compound having activity as an $\alpha_2\delta$ ligand and an intermediate thereof.

BACKGROUND ART

Compounds that exhibit high-affinity binding to voltage-dependent calcium channel subunit $\alpha_2\delta$ have been shown to be effective for treating, for example, neuropathic pain (see e.g., Non-patent Literatures 1 and 2).

Several types of $\alpha_2\delta$ ligands are currently known as therapeutic drugs for neuropathic pain. Examples of $\alpha_2\delta$ ligands include gabapentine and pregabalin. $\alpha_2\delta$ ligands such as these compounds are useful for treating epilepsy and neuropathic pain or the like (e.g., Patent Literature 1). Other compounds are disclosed in, for example, Patent Literatures 2, 3, and 4.

Also, the present applicant has previously reported an $\alpha_2\delta$ ligand and a method for producing the same in Patent Literatures 5 and 6.

CITATION LIST

Patent Literature

Patent Literature 1: US 2006/154929
Patent Literature 2: US 2003/220397
Patent Literature 3: US 2004/152779
Patent Literature 4: US 2003/78300
Patent Literature 5: US 2010/249229
Patent Literature 6: US 2010/110361

Non-Patent Literature

Non-patent Literature 1: J Biol. Chem. 271 (10): 5768-5776, 1996
Non-patent Literature 2: J Med. Chem. 41: 1838-1845, 1998

SUMMARY OF INVENTION

Technical Problem

An object of the present invention is to provide a method for producing a bicyclic γ-amino acid derivative or a pharmacologically acceptable salt thereof, particularly, a compound having activity as an $\alpha_2\delta$ ligand and an intermediate thereof.

While Patent Literature 5 or 6 has reported a production method as described in Scheme 1, the present inventors have continued diligent studies to tackle problems of (1) improving the yields of Step 1 to Step 4, (2) achieving production using more inexpensive starting materials, and (3) facilitating stirring in Step 4 to improve reproducibility. Consequently, the present inventors have solved the problems and completed the present invention.

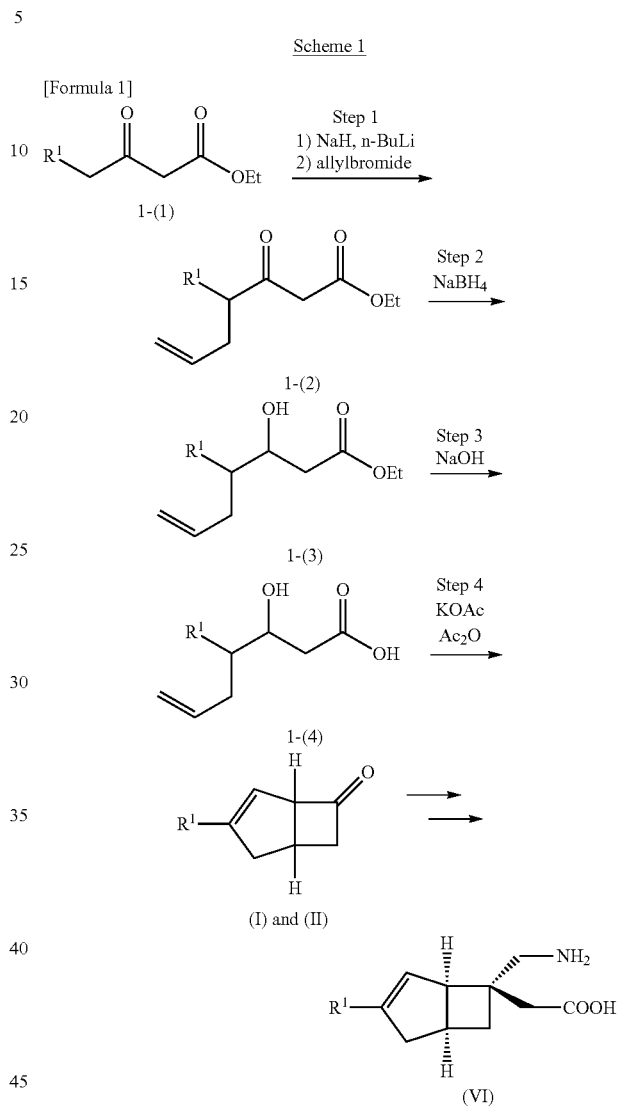

Scheme 1 wherein the substituent is defined as follows: $R^1$: a hydrogen atom or a C1-C6 alkyl group.

Solution to Problem

The present invention will be described below.

[1] A method for producing a compound represented by the general formula (I) and a compound represented by the general formula (II):

[Formula 2]

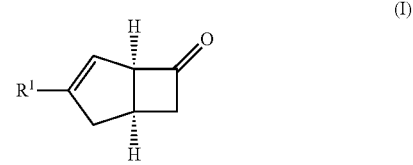

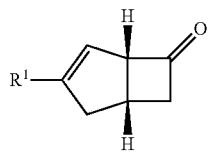

(II)

wherein the substituent is defined as follows: $R^1$: a hydrogen atom or a C1-C6 alkyl group, the method comprising (1) heating a compound represented by the general formula (III) in the presence of an acid anhydride or an acid anhydride and an acid to produce a compound represented by the general formula (IV):

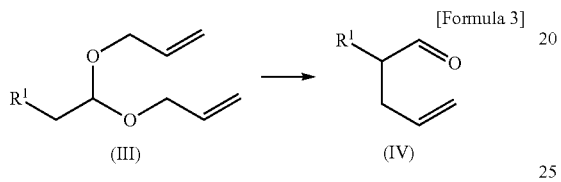

[Formula 3]

wherein the substituent is defined as follows: $R^1$: a hydrogen atom or a C1-C6 alkyl group, (2) heating the compound represented by the general formula (IV) with malonic acid in the presence of a base or a base and a catalyst to produce a compound represented by the general formula (V):

[Formula 4]

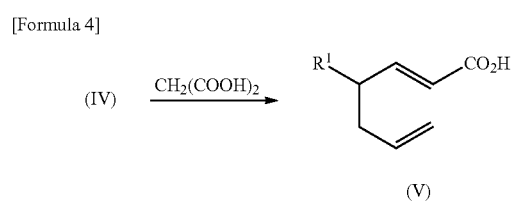

wherein the substituent is defined as follows: $R^1$: a hydrogen atom or a C1-C6 alkyl group, and (3) heating the compound represented by the general formula (V) in the presence of an acid anhydride and a tertiary amine to produce the compound represented by the general formula (I) and the compound represented by the general formula (II).

[2] The method according to [1], wherein $R^1$ is a methyl group, an ethyl group, or a butyl group.

[3] The method according to [1], wherein $R^1$ is an ethyl group.

[4] The method according to any one of [1] to [3], wherein the acid anhydride used in (1) is acetic anhydride.

[5] The method according to any one of [1] to [4], wherein the acid used in (1) is maleic acid.

[6] The method according to any one of [1] to [5], wherein the base used in (2) is pyridine.

[7] The method according to any one of [1] to [6], wherein the catalyst used in (2) is piperidine or morpholine.

[8] The method according to any one of [1] to [7], wherein the acid anhydride and the tertiary amine used in (3) are acetic anhydride and triethylamine, respectively.

[9] A method for producing a compound represented by the general formula (VI) or a salt thereof:

[Formula 5]

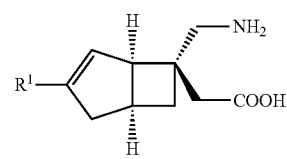

(VI)

wherein the substituent is defined as follows: $R^1$: a hydrogen atom or a C1-C6 alkyl group, the method comprising producing a compound represented by the general formula (I) and a compound represented by the general formula (II) by a method according to [1], and then producing the compound represented by the general formula (VI) or the salt thereof using the compound represented by the general formula (I) and the compound represented by the general formula (II).

Advantageous Effects of Invention

The production method according to the present invention can provide a bicyclic γ-amino acid derivative having excellent activity as an $\alpha_2\delta$ ligand, an intermediate for producing the same, or salts thereof.

The production method of the present invention can produce the compound of interest using only inexpensive starting materials and eliminates the need to use reagents having a high risk of igniting, such as sodium hydride, n-butyllithium, or sodium borohydride. Also, the production method of the present invention can efficiently produce the compound of interest because the method permits continuous production steps without isolating a low-boiling compound and permits reaction in a homogeneous system.

DESCRIPTION OF EMBODIMENTS

A "C1-C6 alkyl group" refers to a linear or branched alkyl group having 1 to 6 carbon atoms and includes methyl, ethyl, propyl, isopropyl, butyl, isobutyl, sec-butyl, tert-butyl, pentyl, isopentyl, 2-methylbutyl, neopentyl, 1-ethylpropyl, hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, and 2-ethylbutyl groups.

(1) Claisen Rearrangement Reaction (Scheme 2)

A compound represented by the general formula (III) is reacted under conditions of Claisen rearrangement reaction to produce a compound represented by the general formula (IV).

Scheme 2

[Formula 6]

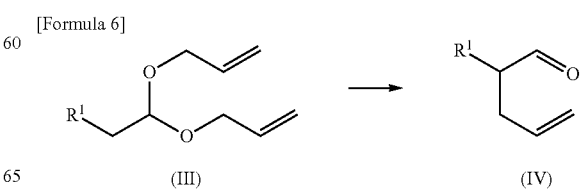

wherein the substituent is defined as follows: R¹: a hydrogen atom or a C1-C6 alkyl group.

The acid anhydride used in this reaction is preferably acetic anhydride, propionic anhydride, butanoic anhydride, succinic anhydride, or the like, more preferably acetic anhydride.

In this reaction, a catalyst might not be used. The addition of an acid in a catalytic amount can promote the reaction. The acid used as a catalyst is preferably a carboxylic acid, more preferably maleic acid.

In this reaction, a solvent might not be used. Use of an aprotic polar solvent such as dimethylacetamide can promote the progression of the reaction.

This reaction can be preferably performed in approximately 10 to 30 hours by heating to approximately 100 to 130° C.

(2) Knoevenagel Condensation Reaction (Doebner Reaction, Scheme 3)

The compound represented by the general formula (IV) is reacted under conditions of Knoevenagel condensation reaction to produce a compound represented by the general formula (V).

Scheme 3

[Formula 7]

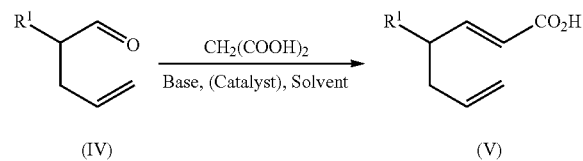

(IV)        (V)

wherein the substituent is defined as follows: R¹: a hydrogen atom or a C1-C6 alkyl group.

The base used in this reaction is preferably pyridine. The addition of, for example, piperidine or morpholine as a catalyst can smoothly promote the reaction.

This reaction proceeds by heating, preferably by heating at 70° C. or higher.

The solvent used in this reaction is preferably pyridine, acetonitrile, or toluene.

(3) [2+2] Cycloaddition Reaction (Scheme 4)

The compound represented by the general formula (V) is reacted under conditions of [2+2] cycloaddition reaction to produce a compound represented by the general formula (I) and a compound represented by the general formula (II).

Scheme 4

[Formula 8]

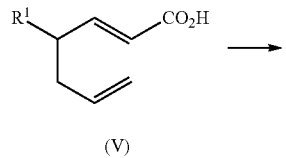

(V)

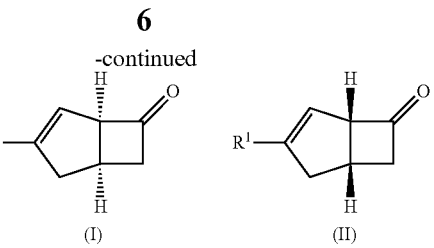

(I)        (II)

wherein the substituent is defined as follows: R¹: a hydrogen atom or a C1-C6 alkyl group.

The acid anhydride used in this reaction is preferably acetic anhydride, propionic anhydride, or butyric anhydride, more preferably acetic anhydride.

The tertiary amine used in this reaction is preferably triethylamine, tripropylamine, tributylamine, or N-methylmorpholine, more preferably triethylamine.

The solvent used in this reaction is preferably an aprotic solvent including N,N-dimethylformamide, N,N-dimethylacetamide, dimethyl sulfoxide, N-methyl-2-pyrrolidone, and 1,3-dimethyl-2-imidazolidinone, more preferably N,N-dimethylacetamide.

This reaction proceeds by heating. The reaction temperature is preferably 100 to 120° C. In this case, the reaction time is 5 to 10 hours.

A compound represented by the general formula (VI) can be produced by the method described in Patent Literature 6 (WO 2010/110361) above using the compound represented by the general formula (I) and the compound represented by the general formula (II).

[Formula 9]

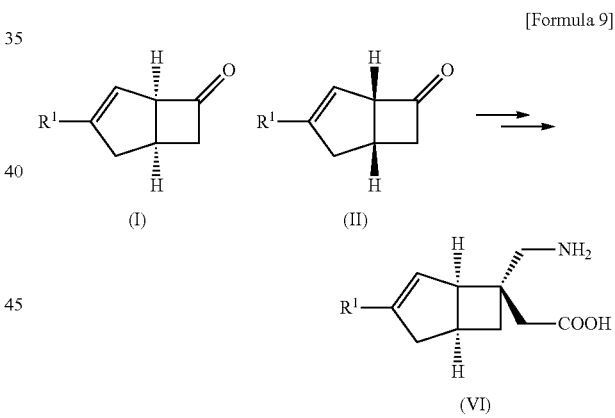

Since compounds represented by the general formula (VI), or the like, having amino and/or carboxyl groups in the structure, forms salts through reaction with an acid or a base, a "salt" as used herein refers to these salts.

The compound represented by the general formula (VI), or the like, when left in the air or recrystallized, may associate with adsorbed water through water absorption to form a hydrate. Such hydrates are also encompassed by the salts of the present invention.

The compound represented by the general formula (VI) or a pharmacologically acceptable salt thereof exhibits activity as an $\alpha_2\delta$ ligand and affinity for voltage-dependent calcium channel subunit $\alpha_2\delta$ and is useful as an active ingredient in a pharmaceutical composition used for treating and/or preventing pain, central nervous system involvement, and other disorders.

EXAMPLES

Example 1

3-Ethylbicyclo[3.2.0]hept-3-en-6-one (1-a) 1,1-Bis(allyloxy)butane

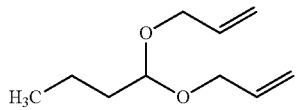

[Formula 10]

Butanal (100 mL, 1.11 mol) and allyl alcohol (100 g, 1.72 mol) were dissolved in hexane (400 mL) under a nitrogen atmosphere. To the solution, magnesium sulfate (82.90 g, 0.69 mol) was added, and the mixture was stirred. This mixture was cooled to 10° C. or lower, and p-toluenesulfonic acid monohydrate (3.28 g, 0.017 mol) was added thereto. The reaction mixture was stirred at 15° C. or lower for 1 hour and warmed to room temperature (approximately 25° C.), followed by further stirring for approximately 2.5 hours. The reaction mixture was cooled again to 10° C. or lower, and potassium carbonate (2.38 g) and water (400 mL) were added thereto in this order. The mixture was stirred until insoluble matter was dissolved. The organic layer was separated and then washed with water (100 mL). The obtained organic layer was concentrated under reduced pressure, and the residue was distilled (approximately 20 mmHg, 80-85° C.) to obtain the title compound (132.83 g, yield: 91%, colorless oil substance).

$^1$H NMR (400 MHz, CDCl$_3$) δ 0.94 (t, 3H, J=7.4 Hz), 1.35-1.45 (m, 2H), 1.61-1.66 (m, 2H), 4.01 (dd, 2H, J=5.6, 12.0 Hz), 4.09 (dd, 2H, J=5.6, 12.0 Hz), 4.61 (t, 1H, J=5.8 Hz), 5.16 (dd, 2H, J=1.6, 10.8 Hz), 5.29 (dd, 2H, J=1.6, 17.2 Hz), 5.92 (ddt, 2H, J=10.8, 17.2, 5.6 Hz).

(1-b) 2-Ethylpent-4-enal

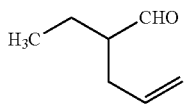

[Formula 11]

1,1-Bis(allyloxy)butane (102.15 g, 0.60 mol) was dissolved in N,N-dimethylacetamide (306 mL) under a nitrogen atmosphere. To the solution, acetic anhydride (170 mL, 1.80 mol) and maleic acid (3.48 g, 0.03 mol) were added, and the mixture was stirred. The reaction mixture was warmed to 120 to 125° C., stirred at this temperature for 24 hours, and then cooled to 10° C. or lower. To the reaction mixture, toluene (410 mL) and water (410 mL) were added, and a 25% aqueous sodium hydroxide solution (586 mL) was slowly added with stirring to separate an organic layer. The aqueous layer was subjected to extraction with toluene (210 mL), and the extract was combined with the organic layer and then washed with water (102 mL) and 20% saline (102 mL) in this order. The organic layer was filtered to remove insoluble matter. Then, the obtained product was used in the next step without being concentrated or purified. The solution of the crude product thus obtained was analyzed by gas chromatography and consequently contained 2-ethylpent-4-enal (58.44 g, yield: 87%).

$^1$H NMR (400 MHz, CDCl$_3$) δ 0.93 (t, 3H, J=7.4 Hz), 1.53-1.61 (m, 1H), 1.64-1.73 (m, 1H), 2.21-2.34 (m, 2H), 2.37-2.44 (m, 1H), 5.04-5.11 (m, 2H), 5.75 (ddt, 1H, J=10.0, 17.2, 7.0 Hz), 9.62 (d, 1H, J=2.0 Hz).

(1-c) (2E)-4-Ethylhepta-2,6-dienoic acid

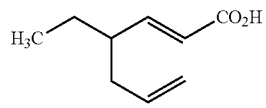

[Formula 12]

Malonic acid (93.74 g, 0.90 mol), acetonitrile (306 mL), morpholine (26 mL, 0.30 mol), and pyridine (97 mL, 1.20 mol) were added in this order to the solution of 2-ethylpent-4-enal (58.44 g) in toluene obtained by the method described above under a nitrogen atmosphere, and the mixture was slowly warmed to approximately 80° C. over approximately 1 hour. After stirring at approximately 80° C. for 13.5 hours, malonic acid (6.24 g, 0.06 mol) was added thereto, and the mixture was further stirred at approximately 80° C. for 3 hours and cooled to room temperature. To the reaction mixture, water (408 mL) was added, and concentrated hydrochloric acid (130 mL) was added to separate an organic layer. The aqueous layer was subjected to extraction with toluene (153 mL), and the extract was combined with the organic layer, followed by two extractions of the compound of interest into aqueous layers using a 2 M aqueous NaOH solution (360 mL×1 and 90 mL×1). The aqueous layers were combined and then adjusted to be acidic by the addition of concentrated hydrochloric acid (80 mL), followed by two extractions with toluene (each with 204 mL). The organic layers were combined and then washed with water (102 mL). The organic layer was concentrated under reduced pressure to obtain the title compound (100.57 g, yellow oil substance).

$^1$H NMR (400 MHz, CDCl$_3$) δ 0.88 (t, 3H, J=7.4 Hz), 1.32-1.42 (m, 1H), 1.50-1.60 (m, 1H), 2.12-2.25 (m, 3H), 5.00-5.06 (m, 2H), 5.65-5.76 (m, 1H), 5.80 (d, 1H, J=15.8 Hz), 6.90 (dd, 1H, J=8.4, 15.8 Hz).

(1-d) 3-Ethylbicyclo[3.2.0]hept-3-en-6-one

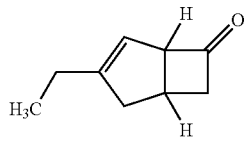

[Formula 13]

(2E)-4-Ethylhepta-2,6-dienoic acid (100.57 g) obtained by the method described above was dissolved in N,N-dimethylacetamide (255 mL) under a nitrogen atmosphere. To the solution, acetic anhydride (108 mL, 1.14 mol) and triethylamine (79 mL, 0.57 mol) were added. The reaction mixture was warmed and stirred at 115 to 117° C. for 5 hours. The reaction mixture was cooled to room temperature, and n-hexane (510 mL) and water (714 mL) were added thereto to separate an organic layer. The aqueous layer was subjected to two extractions with hexane (each with 255 mL), and all the organic layers were combined and then washed with a 5% aqueous sodium bicarbonate solution (102 mL) and water (102 mL) in this order. The obtained organic layer was concentrated under reduced pressure, and the residue was distilled (90-100° C., approximately 25 mmHg) to obtain the title compound (50.92 g, colorless oil substance) (overall yield from 1,1-bis(allyloxy)butane: 62%).

$^1$H NMR (400 MHz, CDCl$_3$) δ 1.07 (t, 3H, J=7.4 Hz), 2.14 (q, 2H, J=7.4 Hz), 2.28-2.34 (m, 1H), 2.75-2.86 (m, 3H), 3.16-3.25 (m, 1H), 4.16-4.22 (m, 1H), 5.20-5.24 (m, 1H).

Example 2

3-Methylbicyclo[3.2.0]hept-3-en-6-one (2-a) 1,1-Bis(allyloxy)propane

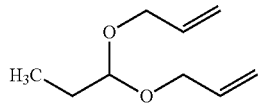

[Formula 14]

Propanal (81 mL, 1.11 mol) and allyl alcohol (100 g, 1.72 mol) were dissolved in hexane (400 mL) under a nitrogen atmosphere. To the solution, magnesium sulfate (82.90 g, 0.69 mol) was added, and the mixture was stirred. This mixture was cooled to 10° C. or lower, and p-toluenesulfonic acid monohydrate (3.28 g, 0.017 mol) was added thereto. The reaction mixture was stirred at 15° C. or lower for 1 hour. To the reaction mixture, potassium carbonate (2.38 g) and water (400 mL) were added in this order. The mixture was stirred until insoluble matter was dissolved. An organic layer was separated and then washed with water (100 mL). The obtained organic layer was concentrated under reduced pressure, and the residue was distilled (approximately 25 mmHg, 67-72° C.) to obtain the title compound (113.67 g, yield: 85%, colorless oil substance).

$^1$H NMR (400 MHz, CDCl$_3$) δ 0.94 (t, 3H, J=7.4 Hz), 1.681 (dq, 2H, J=5.8, 7.4 Hz), 3.99-4.04 (m, 2H), 4.08-4.13 (m, 2H), 4.53 (t, 1H, J=5.8 Hz), 5.15-5.18 (m, 2H), 5.27-5.32 (m, 2H), 5.88-5.98 (m, 2H).

(2-b) 2-Methylpent-4-enal

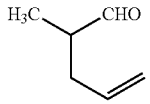

[Formula 15]

1,1-Bis(allyloxy)propane (93.73 g, 0.60 mol) was dissolved in N,N-dimethylacetamide (281 mL) under a nitrogen atmosphere. To the solution, acetic anhydride (170 mL, 1.80 mol) and maleic acid (3.48 g, 0.03 mol) were added, and the mixture was stirred. The reaction mixture was warmed to 115 to 121° C., stirred at this temperature for 24 hours, and then cooled to 10° C. or lower. To the reaction mixture, toluene (380 mL) and water (570 mL) were added, and a 50% aqueous sodium hydroxide solution (294 mL) was slowly added with stirring to separate an organic layer. The aqueous layer was subjected to extraction with toluene (190 mL), and the extract was combined with the organic layer and then washed with 10% saline (190 mL). The organic layer was dried over sodium sulfate. After filtration, the filtrate was used in the next step without being concentrated or purified.

(2-c) (2E)-4-Methylhepta-2,6-dienoic acid

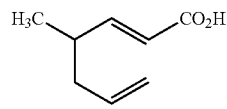

[Formula 16]

Malonic acid (99.90 g, 0.96 mol), acetonitrile (285 mL), morpholine (26 mL, 0.30 mol), and pyridine (97 mL, 1.20 mol) were added in this order to the solution of 2-methylpent-4-enal in toluene obtained by the method described above under a nitrogen atmosphere, and the mixture was warmed to 70 to 80° C. and stirred for approximately 21 hours. The reaction mixture was cooled to room temperature. To the reaction mixture, water (380 mL) was added, and concentrated hydrochloric acid (130 mL) was added to separate an organic layer. The aqueous layer was subjected to extraction with toluene (140 mL), and the extract was combined with the organic layer, followed by extractions into aqueous layers with a 2 M aqueous NaOH solution (358 mL) and a 1.3 M aqueous NaOH solution (134 mL) in this order. The aqueous layers were combined and then adjusted to be acidic by the addition of concentrated hydrochloric acid (80 mL), followed by two extractions with toluene (190 mL and 95 mL). The organic layers were combined and then washed with water (95 mL). The organic layer was concentrated under reduced pressure to obtain the title compound (69.05 g, brown oil substance).

$^1$H NMR (400 MHz, CDCl$_3$) δ 1.08 (d, 3H, J=7.2 Hz), 2.08-2.23 (m, 2H), 2.41-2.48 (m, 1H), 5.02-5.08 (m, 2H), 5.68-5.77 (m, 1H), 5.80 (dd, 1H, J=1.2, 16.0 Hz), 7.02 (dd, 1H, J=7.4, 16.0 Hz).

(2-d) 3-Methylbicyclo[3.2.0]hept-3-en-6-one

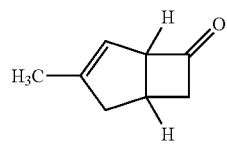

[Formula 17]

(2E)-4-Methylhepta-2,6-dienoic acid (67.74 g) obtained by the method described above was dissolved in N,N-dimethylacetamide (210 mL) under a nitrogen atmosphere. To the solution, acetic anhydride (91 mL, 0.96 mol) and triethylamine (67 mL, 0.48 mol) were added. The reaction mixture was warmed and stirred at 115 to 120° C. for 6 hours. The reaction mixture was cooled to room temperature, and n-hexane (360 mL) and water (540 mL) were added thereto to separate an organic layer. The aqueous layer was subjected to two extractions with hexane (each with 180 mL), and all the organic layers were combined and then washed with a 5% aqueous sodium bicarbonate solution (90 mL) and water (90 mL) in this order. The obtained organic layer was concentrated under reduced pressure, and the residue was distilled (74-76° C., approximately 25 mmHg) to obtain the title compound (39.09 g, colorless oil substance) (overall yield from 1,1-bis(allyloxy)propane: 54%).

$^1$H NMR (400 MHz, CDCl$_3$) δ 1.80 (s, 3H), 2.26-2.32 (m, 1H), 2.72-2.86 (m, 3H), 3.16-3.26 (m, 1H), 4.15-4.23 (m, 1H), 5.20-5.24 (m, 1H).

Example 3

(3-a) 1,1-Bis(allyloxy)hexane

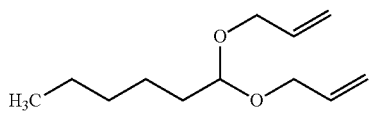

[Formula 18]

Hexanal (138 mL, 1.11 mol) and allyl alcohol (100 g, 1.72 mol) were dissolved in hexane (400 mL) under a nitrogen atmosphere. To the solution, magnesium sulfate (82.90 g, 0.69 mol) was added, and the mixture was stirred. This mixture was cooled to 10° C. or lower, and p-toluenesulfonic acid monohydrate (3.28 g, 0.017 mol) was added thereto. The reaction mixture was stirred at 15° C. or lower for 1 hour. To the reaction mixture, potassium carbonate (2.38 g) and water (400 mL) were added in this order. The mixture was stirred until insoluble matter was dissolved. An organic layer was separated and then washed with water (100 mL). The obtained organic layer was concentrated under reduced pressure, and the residue was distilled (approximately 25 mmHg, 110-118° C.) to obtain the title compound (151.20 g, yield: 89%, colorless oil substance).

$^1$H NMR (400 MHz, CDCl$_3$) δ 0.90 (t, 3H, J=6.8 Hz), 1.26-1.42 (m, 6H), 1.62-1.68 (m, 2H), 4.02 (dd, 2H, J=5.6, 12.8 Hz), 4.11 (dd, 2H, J=5.6, 12.8 Hz), 4.60 (t, 1H, J=5.8 Hz), 5.17 (dd, 2H, J=1.8, 10.6 Hz), 5.29 (dd, 2H, J=1.8, 17.4 Hz), 5.92 (ddt, 2H, J=10.6, 17.4, 5.6 Hz).

(3-b) 2-Allylhexanal

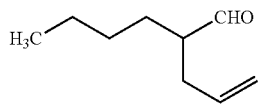

[Formula 19]

1,1-Bis(allyloxy)hexane (118.98 g, 0.60 mol) was dissolved in N,N-dimethylacetamide (320 mL) under a nitrogen atmosphere. To the solution, acetic anhydride (170 mL, 1.80 mol) and maleic acid (3.48 g, 0.03 mol) were added, and the mixture was stirred. The reaction mixture was warmed to 115 to 126° C., stirred at this temperature for 25 hours, and then cooled to 10° C. or lower. To the reaction mixture, toluene (480 mL) and water (720 mL) were added, and a 50% aqueous sodium hydroxide solution (294 mL) was slowly added with stirring to separate an organic layer. The aqueous layer was subjected to extraction with toluene (240 mL), and the extract was combined with the organic layer and then washed with 10% saline (240 mL). The organic layer was dried over sodium sulfate. After filtration, the filtrate was used in the next step without being concentrated or purified.

(3-c) (2E)-4-Allyloct-2-enoic acid

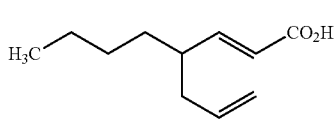

[Formula 20]

Malonic acid (99.90 g, 0.96 mol), acetonitrile (360 mL), morpholine (26 mL, 0.3 mol), and pyridine (97 mL, 1.2 mol) were added in this order to the solution of 2-allylhexanal in toluene obtained by the method described above under a nitrogen atmosphere, and the mixture was slowly warmed to 72 to 82° C. over 1 hour and 20 minutes and stirred at this temperature for approximately 24 hours. The reaction mixture was cooled to room temperature. To the reaction mixture, water (480 mL) was added, and concentrated hydrochloric acid (130 mL) was added to separate an organic layer. The aqueous layer was subjected to extraction with toluene (180 mL), and the extract was combined with the organic layer, followed by extractions into aqueous layers with a 2 M aqueous NaOH solution (358 mL) and a 1.3 M aqueous NaOH solution (134 mL) in this order. The aqueous layers were combined and then adjusted to be acidic by the addition of concentrated hydrochloric acid (80 mL), followed by two extractions with toluene (240 mL and 180 mL). The organic layers were combined and then washed with water (120 mL). The organic layer was concentrated under reduced pressure to obtain the title compound (99.11 g, brown oil substance).

$^1$H NMR (400 MHz, CDCl$_3$) δ 0.88 (t, 3H, J=7.2 Hz), 1.16-1.39 (m, 5H), 1.45-1.54 (m, 1H), 2.09-2.36 (m, 3H), 5.00-5.05 (m, 2H), 5.65-5.76 (m, 1H), 5.79 (d, 1H, J=15.6 Hz), 6.90 (dd, 1H, J=8.6, 15.6 Hz).

(3-d) 3-Butylbicyclo[3.2.0]hept-3-en-6-one

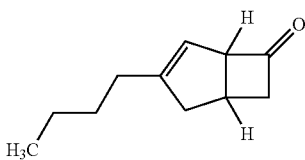

[Formula 21]

(2E)-4-Allyloct-2-enoic acid (99.10 g) obtained by the method described above was dissolved in N,N-dimethylacetamide (297 mL) under a nitrogen atmosphere. To the solution, acetic anhydride (103 mL, 1.09 mol) and triethylamine (76 mL, 0.55 mol) were added. The reaction mixture was warmed and stirred at 115 to 120° C. for 6 hours. The reaction mixture was cooled to room temperature. To the reaction mixture, n-hexane (480 mL) and water (720 mL) were added to separate an organic layer. The aqueous layer was subjected to two extractions with hexane (each with 240 mL), and all the organic layers were combined and then washed with a 5% aqueous sodium bicarbonate solution (120 mL) and water (120 mL) in this order. The obtained organic layer was concentrated under reduced pressure, and the residue was distilled (120-128° C., approximately 25 mmHg) to obtain the title compound (61.95 g) (overall yield from 1,1-bis(allyloxy)hexane: 63%).

¹H NMR (400 MHz, CDCl₃) δ 0.91 (t, 3H, J=7.4 Hz), 1.31 (tq, 2H, J=7.4, 7.4 Hz), 1.41-1.49 (m, 2H), 2.13 (t, 2H, J=7.6 Hz), 2.28-2.34 (m, 1H), 2.73-2.86 (m, 3H), 3.16-3.25 (m, 1H), 4.15-4.23 (m, 1H), 5.21-5.25 (m, 1H).

Reference Example 1

[6-Aminomethyl-3-ethylbicyclo[3.2.0]hept-3-en-6-yl]acetic acid

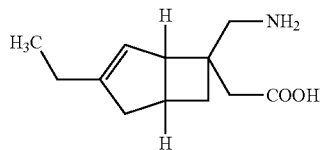

[Formula 22]

(1-a) Ethyl 4-ethyl-3-hydroxyhept-6-enoate

Sodium hydride (>63% oil, 2.09 g, 55 mmol) was added to a solution of ethyl 3-oxohexanoate (7.91 g, 50 mmol) in tetrahydrofuran (50 mL) under ice cooling, and the mixture was stirred in this state for 10 minutes. To the reaction solution, n-butyllithium (1.58 M solution in hexane, 34.8 mL, 55 mmol) was added dropwise, and the mixture was further stirred for 10 minutes under ice cooling. Then, allyl bromide (4.7 mL, 55 mmol) was added thereto, and the mixture was stirred in this state for 1 hour and then further stirred at room temperature for 4 hours. To the reaction solution, 1 N hydrochloric acid and a saturated aqueous solution of ammonium chloride were added, followed by extraction with n-pentane. The organic layer was washed with saturated saline and dried over anhydrous magnesium sulfate, and the solvent was distilled off under reduced pressure. The obtained residue was dissolved in ethanol (80 mL). To the solution, sodium borohydride (1.51 g, 40 mmol) was added under ice cooling, and the mixture was stirred in this state for 2 hours. 1 N hydrochloric acid (50 mL) was added thereto, and the mixture was stirred for 30 minutes. Then, saturated saline was added thereto, followed by extraction with ethyl acetate. The organic layer was washed with saturated saline and then dried over anhydrous magnesium sulfate, and the solvent was distilled off under reduced pressure. The residue was purified by silica gel column chromatography to obtain the compound of interest as a pale yellow oil substance (3.64 g, 37%, mixture of diastereomers).

¹H-NMR (400 MHz, CDCl₃): δ ppm: 0.91 (3H, t, J=7.5 Hz), 1.28 (3H, t, J=7.2 Hz), 1.43-1.55 (2H, m), 1.98-2.28 (2H, m), 2.45-2.48 (2H, m), 2.88-2.93 (1H, m), 4.07-4.10 (1H, m), 4.10-4.20 (2H, m), 5.01-5.09 (2H, m), 5.75-5.86 (1H, m).

(1-b) 4-Ethyl-3-hydroxyhept-6-enoic acid

Ethyl 4-ethyl-3-hydroxyhept-6-enoate (3.64 g, 18.2 mmol) was dissolved in a 2 N solution of potassium hydroxide in methanol (120 mL), and the solution was stirred overnight at room temperature. From the reaction solution, the solvent was distilled off under reduced pressure. To the residue, a 1 N aqueous sodium hydroxide solution (200 mL) was then added, followed by extraction with diethyl ether. The aqueous layer was made acidic by the addition of concentrated hydrochloric acid under ice cooling, followed by extraction with diethyl ether again. The organic layer was washed with saturated saline and dried over anhydrous magnesium sulfate. Then, the solvent was distilled off under reduced pressure to obtain the compound of interest as a pale yellow oil substance (3.14 g, <100%, mixture of diastereomers).

¹H-NMR (400 MHz, CDCl₃): δ ppm: 0.91-0.96 (3H, m), 1.39-1.52 (3H, m), 2.01-2.28 (2H, m), 2.52-2.55 (2H, m), 4.05-4.15 (2H, m), 5.03-5.10 (2H, m), 5.74-5.86 (1H, m).

(1-c) Tert-butyl 3-ethylbicyclo[3.2.0]hept-3-en-6-ylideneacetate

4-Ethyl-3-hydroxyhept-6-enoic acid (3.13 g, 18.2 mmol) was dissolved in acetic anhydride (15 mL). To the solution, potassium acetate (4.27 g, 43.6 mmol) was added, and the mixture was stirred at room temperature for 100 minutes. The reaction solution was heated to reflux and stirred for 3.5 hours to form "3-ethylbicyclo[3.2.0]hept-6-en-6-one" in the reaction solution. To the reaction solution, ice water and toluene were then added, and this mixture was stirred overnight at room temperature. The mixture was separated into aqueous and organic layers by the addition of saturated saline (50 mL) and toluene (20 mL). Then, the organic layer was washed with a 1 N aqueous sodium hydroxide solution and saturated saline in this order, then dried over anhydrous magnesium sulfate, and filtered. The filtrate was added to a reaction solution prepared by adding sodium hydride (>65% oil, 761.9 mg, 20 mmol) to a solution of tert-butyl dimethoxyphosphorylacetate (4.48 g, 20 mmol) in tetrahydrofuran (50 mL) under ice cooling, and the mixture was further stirred for 1 hour. The reaction solution was separated into aqueous and organic layers by the addition of a saturated aqueous solution of ammonium chloride and saturated saline. The aqueous layer was subjected to extraction with ethyl acetate. The organic layers were combined, then washed with saturated saline, and then dried over anhydrous magnesium sulfate. The solvent was distilled off under reduced pressure, and the residue was purified by silica gel column chromatography to obtain the compound of interest as a pale yellow oil substance (1.32 g, 31%, E/Z mixture).

¹H-NMR (400 MHz, CDCl₃): δ ppm:

Major isomer: 1.06 (3H, t, J=7.4 Hz), 1.45 (9H, s), 2.07-2.22 (3H, m), 2.59-2.70 (2H, m), 2.87-2.96 (1H, m), 3.30 (1H, ddt, J=8.6, 18.4, 2.7 Hz), 3.86-3.88 (1H, m), 5.22-5.23 (1H, m), 5.45-5.47 (1H, m).

Minor isomer: 1.08 (3H, t, J=7.3 Hz), 1.49 (9H, s), 2.07-2.21 (3H, m), 2.43-2.47 (1H, m), 2.59-2.70 (1H, m), 2.75-2.85 (1H, m), 2.87-2.96 (1H, m), 4.28-4.31 (1H, m), 5.35-5.38 (1H, m), 5.45-5.47 (1H, m).

(1-d) Tert-butyl [3-ethyl-6-(nitromethyl)bicyclo[3.2.0]hept-3-en-6-yl]acetate

Tert-butyl 3-ethylbicyclo[3.2.0]hept-3-en-6-ylideneacetate (1.32 g, 5.63 mmol) was dissolved in nitromethane (7 mL). To the solution, 1,8-diazabicyclo[5.4.0]undec-7-ene (1.2 mL, 7.3 mmol) was added, and the mixture was heated with stirring at 50 to 60° C. for 7 hours. The mixture was allowed to cool, and a saturated aqueous solution of potassium dihydrogen phosphate was then added thereto, followed by extraction with ethyl acetate. Then, the organic layer was dried over anhydrous magnesium sulfate, and the solvent was distilled off under reduced pressure. The residue was purified by silica gel column chromatography to obtain the compound of interest as a colorless oil substance (1.39 g, 84%).

¹H-NMR (400 MHz, CDCl₃): δ ppm: 1.09 (3H, t, J=7.4 Hz), 1.46 (9H, s), 1.52 (1H, dd, J=7.6, 13.2 Hz), 2.06 (1H,d, 16.6 Hz), 2.14 (2H, q, J=7.4 Hz), 2.30 (1H, ddd, J=2.4, 7.6, 13.2 Hz), 2.47 (2H, s), 2.49 (1H, dd, J=7.6,16.6 Hz), 2.86 (1H, quint, J=7.6 Hz), 3.21-3.22 (1H, m), 4.75 (1H, d, J=11.7 Hz), 4.84 (1H, d, J=11.7 Hz), 5.27 (1H, s).

(1-e) [6-Aminomethyl-3-ethylbicyclo[3.2.0]hept-3-en-6-yl]acetic acid

Tert-butyl [3-ethyl-6-(nitromethyl)bicyclo[3.2.0]hept-3-en-6-yl]acetate (1.09 g, 4.71 mmol) was dissolved in ethanol (10 mL) and water (5 mL). To the solution, iron powder (1.32 g, 23.5 mmol) and ammonium chloride (249.6 mg, 4.71 mmol) were added, and the mixture was stirred for 2 hours under heating to reflux. The mixture was allowed to cool, then diluted with saturated saline, a saturated aqueous solution of sodium bicarbonate, and ethyl acetate, and filtered through Celite to remove insoluble matter. The filtrate was separated into organic and aqueous layers. The organic layer was washed with saturated saline and then dried over anhydrous magnesium sulfate, and the solvent was then distilled off under reduced pressure. To the residue, a 4 N solution of hydrochloric acid in ethyl acetate (20 mL) was added, and the mixture was stirred at room temperature for 1 hour. Then, the solvent was distilled off under reduced pressure. The residue was suspended in dichloromethane. To the suspension, triethylamine was added dropwise, and the resulting powder was collected by filtration, then washed with dichloromethane, and then dried to obtain the compound of interest as a white powder (425.1 mg, 43%).

$^1$H-NMR (400 MHz, CD$_3$OD): δ ppm: 1.10 (3H, t, J=7.4 Hz), 1.48 (1H, dd, J=7.5, 12.5 Hz), 2.03-2.08 (2H, m), 2.14 (2H, q, J=7.4 Hz), 2.46 (1H, d, J=16.2 Hz), 2.46-2.53 (1H, m), 2.51 (1H, d, J=16.2 Hz), 2.85 (1H, quint, J=7.5 Hz), 3.09-3.10 (1H, m), 3.14 (1H, d, J=13.0 Hz), 3.18 (1H, d, J=13.0 Hz), 5.38 (1H, dd, J=1.7, 3.7 Hz).

(Step of Performing Optical Resolution from Diastereomeric Mixture)

Reference Example 2

Tert-butyl [(1R,5S,6S)-6-aminomethyl-3-ethylbicyclo[3.2.0]hept-3-en-6-yl]acetate D-mandelate

[Formula 23]

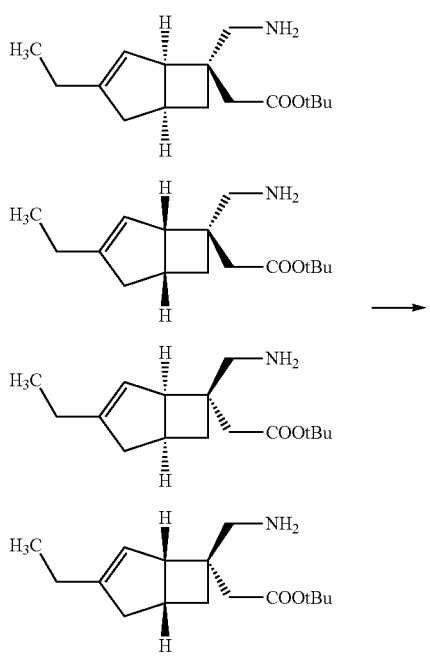

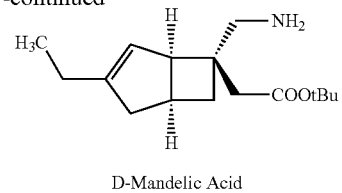

D-Mandelic Acid

Acetonitrile (4.7 L, 8.6 v/w) was added to tert-butyl [6-aminomethyl-3-ethylbicyclo[3.2.0]hept-3-en-6-yl]acetate (627.0 g, net: 543.6 g, 2.05 mol, 85:15 diastereomeric mixture), and the mixture was stirred at 40° C. To the reaction solution, D-mandelic acid (116.3 g, 0.76 mmol, 0.37 eq.) was added, and the mixture was stirred at 40° C. for 1 hour and then allowed to cool slowly to 3° C. After stirring at 3° C. for 1 hour, the resulting crystal was collected by filtration. Then, the crystal was dried under reduced pressure under the condition of 40° C. to obtain tert-butyl [(1R,5S,6S)-6-aminomethyl-3-ethylbicyclo[3.2.0]hept-3-en-6-yl]acetate D-mandelate as a white powder (251.2 g, yield: 29.4%, 97.6% ee, 99.6% de).

$^1$H-NMR (400 MHz, DMSO-d6) δ ppm: 1.04 (3H, t, J=7.6 Hz), 1.28-1.35 (1H, m), 1.39 (9H, s), 1.96-2.11 (4H, m), 2.28 (1H, d, J=15.6 Hz), 2.33 (1H, d, J=15.6 Hz), 2.36-2.40 (1H, m), 2.72 (1H, quint, J=7.6 Hz), 3.00 (1H, d, J=13.2 Hz), 3.03 (1H, d, J=13.2 Hz), 3.31 (1H, br s), 4.54 (1H, s), 5.21-5.23 (1H, m), 7.13-7.25 (3H, m), 7.35-7.37 (2H, m).

$[α]_{20}^D$ −104.4° (C=0.108, MeOH).

Anal. calcd for C$_{24}$H$_{35}$NO$_5$: C, 69.04; H, 8.45; N, 3.35; Found C, 69.15; H, 8.46; N, 3.46.

The invention claimed is:

1. A method for producing a compound of general formula (I) and a compound of general formula (II):

comprising:
(1) heating a compound of general formula (III) in the presence of an acid anhydride or an acid anhydride and an acid to produce a compound of general formula (IV):

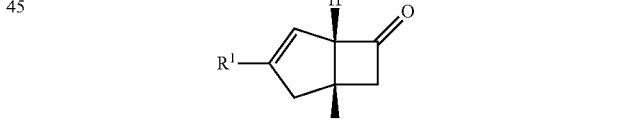

(2) heating the compound of general formula (IV) with malonic acid in the presence of a base or a base and a catalyst to produce a compound of general formula (V):

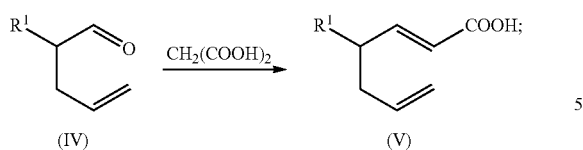

and
(3) heating the compound of general formula (V) in the presence of an acid anhydride and a tertiary amine to produce the compound of general formula (I) and the compound of general formula (II);
wherein $R^1$ is hydrogen or a C1-C6 alkyl group.

2. The method of claim 1, wherein $R^1$ is a methyl group, an ethyl group, or a butyl group.

3. The method of claim 1, wherein $R^1$ is an ethyl group.

4. The method of claim 1, wherein the acid anhydride of each of (1) and (3) is acetic anhydride.

5. The method of claim 1, wherein the acid is maleic acid.

6. The method of claim 1, wherein the base is pyridine.

7. The method of claim 1, wherein, in step (2), the heating of the compound of general formula (IV) is in the presence of a base and a catalyst, and the catalyst is piperidine or morpholine.

8. The method of claim 1, wherein the acid anhydride of each of (1) and (3) is acetic anhydride and the tertiary amine is triethylamine.

* * * * *